United States Patent [19]

Kotick et al.

[11] 4,440,932

[45] Apr. 3, 1984

[54] 7β-ARYLALKYL-7α-METHYL-6-OXO OR 6α-HYDROXY-3-METHOXY OR 3-HYDROXY-4,5α-EPOXY-17-METHYL OR 17-CYCLOALKYL-METHYLMORPHINANS

[75] Inventors: Michael P. Kotick; David L. Leland, both of Elkhart, Ind.

[73] Assignee: Miles Laboratories, Inc., Elkhart, Ind.

[21] Appl. No.: 416,145

[22] Filed: Sep. 9, 1982

[51] Int. Cl.³ .................. C07D 489/02; A61K 31/485
[52] U.S. Cl. ..................................... 546/44; 424/260; 546/39; 546/45
[58] Field of Search ............................ 546/44, 45, 46; 424/260

[56] References Cited

U.S. PATENT DOCUMENTS

| | | | |
|---|---|---|---|
| 2,178,010 | 10/1939 | Small et al. | 546/74 |
| 4,275,205 | 6/1981 | Kotick et al. | 546/44 |
| 4,347,361 | 8/1982 | Quick et al. | 546/45 |

OTHER PUBLICATIONS

Kotick et al., J. Med. Chem., 24(12), pp. 1445–1450, (1981).
Stork, "The Alkaloids", vol. VI, Manske, ed., Academic Press, N.Y., (1960), p. 226.
Quick et al., J. Med. Chem., 25(8), pp. 983–986, (1982).
Leland et al., J. Org. Chem., 48(11), pp. 1813–1819, (1983).

Kotick et al., J. Med. Chem., 26(7), pp. 1050–1056, (1983).

*Primary Examiner*—David G. Daus
*Assistant Examiner*—Diana G. Rivers
*Attorney, Agent, or Firm*—Jerome L. Jeffers

[57] ABSTRACT

Disclosed are 7β-arylalkyl-7α-methyl-6-oxo or 6α-hydroxy-3-methoxy or 3-hydroxy-4,5α-epoxy-17-methyl or 17-cycloalkylmethyl-morphinans of the formula:

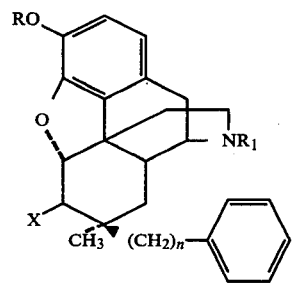

wherein R is H or methyl, X is oxo or α-hydroxy, n is 2 to 4 and $R_1$ is methyl, cyclopropylmethyl or cyclobutylmethyl. These compounds are useful as strong analgesics.

10 Claims, No Drawings

7β-ARYLALKYL-7α-METHYL-6-OXO OR 6α-HYDROXY-3-METHOXY OR 3-HYDROXY-4,5α-EPOXY-17-METHYL OR 17-CYCLOALKYL-METHYLMORPHINANS

BACKGROUND OF THE INVENTION

Morphine is a well-known narcotic analgesic having a structure formula:

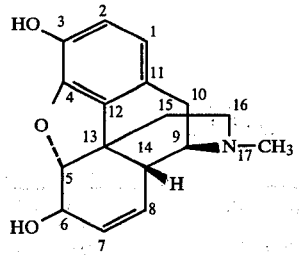

The compounds of this invention are structurally related to morphine and are named according to the morphinan system of nomenclature using the morphinan nucleus as shown below:

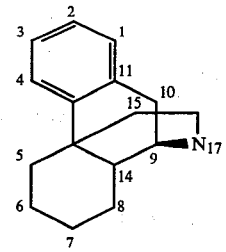

The numbering and the stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for the morphine nucleus unless otherwise indicated.

In U.S. Pat. No. 4,275,205, there is disclosed 7,7-ditosyloxymethyl-4,5α-epoxy-3-methoxy-17-methyl-morphinan-6β-ols of the formula:

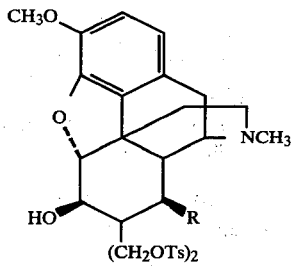

where R is H, CH₃ or CH₂CH₃. These compounds are precursors for certain 7,7-dimethyl-morphinans having analgesic activity or a combination of analgesic and narcotic antagonist activity.

SUMMARY OF THE INVENTION

The present invention involves 3,7-substituted-6-oxo or 6α-hydroxy-4,5α-epoxy morphinans of the formula:

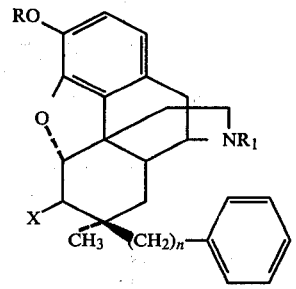

wherein R is H or methyl, X is oxo or α-hydroxy, n is 2 to 4 and $R_1$ is methyl, cyclopropylmethyl or cyclobutylmethyl.

DESCRIPTION OF THE INVENTION

Referring to scheme I, the N-methyl or N-cycloalkyl-methyl-6α,7α-oxymethylene compounds A (prepared as described in co-pending application Ser. No. 403,464, filed on July 20, 1982 by Michael P. Kotick, et al) are cleaved to the 6α-hydroxy-7α-methyl compounds B by refluxing with a 3:1 mixture of lithium aluminum hydride-aluminum chloride in ether for 18 hours. The 6α-hydroxy group of B is then oxidized to the ketone (compound C) by use of dimethylsulfoxidetrifluoroacetic anhydride. The 3-methoxy compounds C are converted to 3-hydroxy compounds D using refluxing 48% hydrobromic acid.

SCHEME I

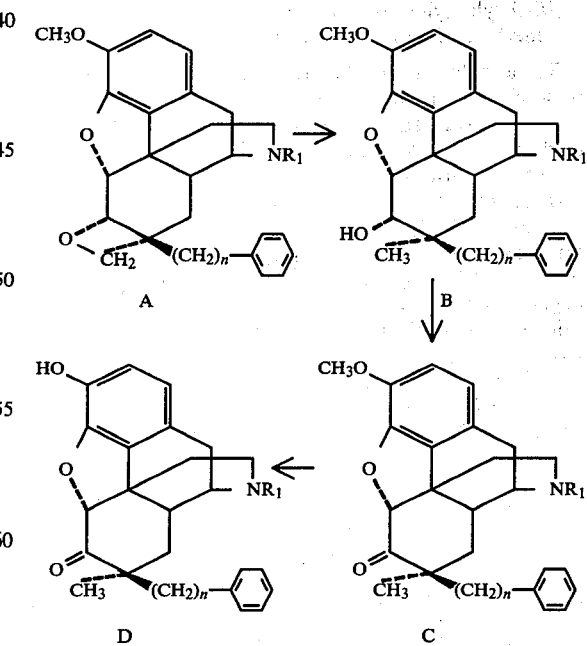

$R_1 = P = $ cyclopropylmethyl
$R_1 = B = $ cyclobutylmethyl
$R_1 = M = $ methyl -continued
SCHEME I d, n = 2
e, n = 3
f, n = 4

The novel morphinan compounds disclosed herein are prepared as described by the following examples where the letter designations correspond with scheme I.

EXAMPLE I

7β-Arylalkyl-17-(cycloalkylmethyl)-4,5α-epoxy-3-methoxy-7α-methylmorphinan-6α-ols (BP, BB)

A suspension of AlCl$_3$ (1.95 g, 14.6 mmole) in Et$_2$O (100 ml) was cooled in an ice bath and LiAlH$_4$ (1.66 g, 43.9 mmole) added. After stirring for 30 minutes, a solution of 7β-phenylbutyl-17-(cyclopropylmethyl)-4,5α-epoxy-3-methoxy-6α,7α-(oxymethylene) morphinan (7.1 g, 14.6 mmole) in Et$_2$O (250 ml) was added and the mixture refluxed for 18 hours. The cooled mixture was treated sequentially dropwise with H$_2$O (1.7 ml), 15% NaOH (1.7 ml) and H$_2$O (5.1 ml), then filtered through Celite. The filtrate was diluted with EtOAc and washed with H$_2$O. Evaporation gave 5.8 g of a glass which was chromatographed to give 4.43 g (62%) of BPf as a glass. A portion of this material was converted to the HCl salt, which was obtained as white crystals, mp 118°–122° C., from EtOAc. Several recrystallizations from EtOAc gave analytically pure material with an indefinite mp. Anal. (C$_{32}$H$_{41}$NO$_3$.HCl). In a similar manner, BBd was obtained as a foam in 84% yield. Crystals of the HCl salt, mp 169°–171° C., were obtained from EtOAc. Anal. (C$_{31}$H$_{39}$NO$_3$.HCl). Compound BBf was obtained in 65% yield and crystallized as the HCl salt, mp sinters 116°, melts 123°–130° C. Anal. (C$_{33}$H$_{43}$NO$_3$.HCl).

EXAMPLE II

7β-Arylalkyl-17-(cycloalkylmethyl)-4,5α-epoxy-3-methoxy-7α-methylmorphinan-6-one (CP, CB)

To a solution of dimethylsulfoxide (1.0 ml, 14.3 mmole) in methylene chloride (CH$_2$Cl$_2$) under argon at −60° C., was added dropwise, trifluoroacetic anhydride (1.5 ml, 10.7 mmole) in CH$_2$Cl$_2$ (7 ml). After 10 minutes, a solution of BPf (3.48 g, 7.1 mmole) in CH$_2$Cl$_2$ (50 ml) was added slowly. The mixture was kept at −60° C. for 90 minutes, then triethylamine (3 ml) was added and the mixture warmed to room temperature. After washing with H$_2$O, evaporation of the organic phase gave 3.47 g of CPf as a foam. The HCl salt, mp 105°–110° C., was recrystallized several times from EtOAc and best analyzed as containing 0.33 mmole EtOAc. Anal. (C$_{32}$H$_{39}$NO$_3$.HCl.0.33 EtOAc). The free base of CBc was obtained as crystals, mp 150°–151° C., in 77% yield after chromatography and crystallization from EtOAc-Et$_2$O. Anal. (C$_{31}$H$_{37}$NO$_3$). Compound CBf was obtained in quantitative yield as crystals, mp 149°–152° C. Recrystallization from EtOAc gave 96% yield of pure CBf, mp 150°–151.5° C. Anal. (C$_{33}$H$_{41}$NO$_3$) C, H, N.

EXAMPLE III

7β-Arylalkyl-17-(cycloalkylmethyl)-4,5α-epoxy-3-hydroxy-7α-methyl-morphinan-6-ones (DP, B)

A mixture of the appropriate compound C from example II and 48% HBr was refluxed for 15 minutes, the mixture cooled and diluted with H$_2$O. The solution was made basic by the addition of NH$_4$OH and extracted with chloroform (CHCl$_3$). Evaporation was followed by chromatography of the residue. Chromatography gave DBf in 63% yield as a foam. Crystals of DPf, mp 183.5°–185° C., were deposited from EtOAc. Anal. (C$_{31}$H$_{37}$NO$_3$). Compound DBc was obtained in 42% yield after chromatography. The HCl salt, mp sinters above 200° C., crystallized from EtOAc. Anal. (C$_{30}$H$_{35}$NO$_3$.HCl). The foam obtained upon workup of DBf crystallized upon titration with EtOAc. These crystals, obtained in 53% yield, were recrystallized from EtOAc to give pure DBf, mp 186°–188.5° C. Anal. (C$_{32}$H$_{39}$NO$_3$).

ELEMENTAL ANALYSES

| Compound | Formula | % C | % H | % N | |
|---|---|---|---|---|---|
| BPf | C$_{32}$H$_{41}$NO$_3$.HCl | 73.33 | 8.08 | 2.67 | Calc. |
| | | 73.22 | 8.20 | 2.61 | Found |
| BBd | C$_{31}$H$_{39}$NO$_3$.HCl | 72.99 | 7.90 | 2.75 | |
| | | 73.06 | 8.09 | 2.83 | |
| BBf | C$_{33}$H$_{43}$NO$_3$.HCl | 73.65 | 8.24 | 2.60 | |
| | | 73.56 | 8.21 | 2.52 | |
| CPf | C$_{32}$H$_{39}$NO$_3$.HCl.0.33 EtOAc | 72.60 | 7.80 | 2.54 | |
| | | 72.43 | 7.44 | 2.68 | |
| CBd | C$_{31}$H$_{37}$NO$_3$ | 78.94 | 7.91 | 2.97 | |
| | | 78.95 | 8.08 | 2.81 | |
| CBf | C$_{33}$H$_{41}$NO$_3$ | 79.32 | 8.27 | 2.80 | |
| | | 79.45 | 8.15 | 2.67 | |
| DPf | C$_{31}$H$_{37}$NO$_3$ | 78.95 | 7.91 | 2.97 | |
| | | 78.89 | 7.89 | 2.69 | |
| DBd | C$_{30}$H$_{35}$NO$_3$.HCl | 72.93 | 7.34 | 2.84 | |
| | | 73.21 | 7.59 | 2.63 | |
| DBf | C$_{32}$H$_{39}$NO$_3$ | 79.14 | 8.09 | 2.88 | |
| | | 79.17 | 8.11 | 2.72 | |

EXAMPLE IV

7α,17-Dimethyl-4,5α-epoxy-3-methoxy-7β-(4-phenylbutyl)morphinan-6α-ol (BMf)

To a suspension of AlCl$_3$ (1.29 g, 9.6 mmole) in Et$_2$O (100 ml) under argon, cooled in an ice bath, was added LiAlH$_4$ (1.10 g, 28.9 mmole). The mixture was stirred for 30 min. in the bath after which a solution of 4,5α-epoxy-3-methoxy-17-methyl-7β-(4-phenylbutyl)-6α,7α-(oxymethylene)morphinan (4.20 g, 9.4 mmole) in Et$_2$O (200 ml) was added. The mixture was then refluxed for 2 days. The reaction mixture was quenched by the addition of H$_2$O and 3 N NaOH. After filtration from insoluble material, the filtrate was evaporated and the residue diluted with H$_2$O and extracted with EtOAc. Processing in the usual fashion followed by chromatography gave 2.41 g (57%) of BMf as a glass. Crystallization of a portion of this material from EtOAc-hexane gave crystals, mp 90°–93° C. Drying at 35° C. in high vacuum gave crystals with mp 89°–92° C. which were shown by NMR to be the 0.25 solvate of BMf with hexane: NMR δ 7.22 (s, 5H, phenyl); 6.63 (s, 2H, H1 and H2); 4.72 (d, 1H, H5, J=5 Hz); 3.85 (CH$_3$O—); 3.62 (d, 1H, H6); 0.87 (s, 7α CH$_3$—).

Anal. Calcd. for C$_{29}$H$_{37}$NO$_3$.0.25 C$_6$H$_{14}$: C, 78.08; H, 8.70; N, 2.99. Found: C, 77.75; H, 9.04; N, 2.99.

EXAMPLE V

7α,17-Dimethyl-4,5α-epoxy-3-methoxy-7β-(4-phenylbutyl)morphinan-6-one (CMf)

A mixture of DMSO (9.6 mmole) and TFAA (7.2 mmole) in CH$_2$Cl$_2$ (15 ml) was prepared as above at −60° C. To this was added BMf (2.14 g, 4.78 mmole) in CH2Cl2 (70 ml) and the reaction conducted in the usual fashion for 90 min. After the addition of TEA (2 ml) and processing in the usual manner, chromatography gave 1.79 g (84%) of CMf as a glass: NMR δ 7.18 (broad, s, 5H); 6.61 (s, 2H); 4.76 (s, 1H, H5); 3.92 (CH3O—); 2.43 (CH3N—); 0.88 (s, 3H, 7α CH3—). A portion of this material was converted to the HCl salt which gave crystals, mp 224°–226° C., from EtOAc.

Anal. Calcd. for $C_{29}H_{35}NO_3$·HCl: C, 72.26; H, 7.53; N, 2.90. Found: C, 71.86; H, 7.51; N, 2.74.

EXAMPLE VI

7α,17-Dimethyl-4,5α-epoxy-3-hydroxy-7β-(4-phenylbutyl)morphinan-6-one (DMf)

A solution of CMf.HCl (1.43 g, 2.97 mmole) in CHCl3 (60 ml) was added to a solution of BBr3 (1.82 ml, 19.2 mmole) in CHCl3 (40 ml) cooled in an ice bath under argon. The mixture was stirred for 30 min. at ambient temperature, then recooled to 0° C. and MeOH (5 ml) added dropwise. The resulting mixture was evaporated, the residue dissolved in H2O and excess concentrated NH4OH added. Processing with CHCl3 gave 1.30 g of a foam which was chromatographed to give 0.87 g of recovered CMf followed by 0.50 g (39%) of DMf as a glass: NMR δ 4.70 (s, H5); 2.46 (CH3N—); 0.88 (s, 7α CH3—). This was converted to the HCl salt which crystallized from MeOH-EtOAc to give 22.HCl, mp >265° C.

Anal. Calcd. for C, 71.86; H, 7.32; N, 2.99. Found: C, 71.46; H, 7.16; N, 2.80.

PHARMACOLOGICAL EVALUATION

Analgesic effects of the test compounds were determined in mice by use of the acetic acid induced writhing test described by B. A. Whittle, *Brit. J. Pharmacol.*, 22:246 (1964). In this test, at least 3 groups of 5 male CD-1 mice each were given subcutaneous doses of the test drug dissolved in distilled water. In all cases, 0.4 ml of a 0.5% v/v acetic acid in distilled water solution was administered intraperitoneally 15 min. post drug. The number of writhes in a 20 min. interval beginning 5 min. after the acetic acid injection were determined and compared with the number of writhes in a control group which had received only acetic acid.

Percent inhibition of writhing was calculated as:

$$\% \text{ inhibition} = \frac{\text{No. Control Writhes} - \text{No. Treated Writhes}}{\text{No. Control Writhes}}$$

The $ED_{50}$ dose, i.e., the dose required to reduce the number of writhes by 50%, was determined graphically from a plot of % inhibition as a probit verus log dose. Confidence limits of 95% were calculated on the basis of those results falling in the range 16–84% inhibition. See Lichtfield, J. T. and Wilcoxon, F., *J. Pharmacol. Exp. Ther.*, 96, 99–113 (1949).

The results of this evaluation are set out in table I.

TABLE I

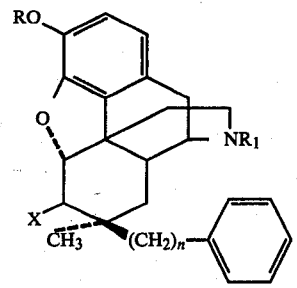

| Compound | R | R1 | N | X | $ED_{50}$ (μmole/kg) | $ED_{50}$ (mg/kg) |
|---|---|---|---|---|---|---|
| BPf[a] | CH3 | P | 4 | OH | 0.50 | 0.26 |
| BBd[a] | CH3 | B | 2 | OH | 1.0 | 0.51 |
| BBf[a] | CH3 | B | 4 | OH | 11.3 | 6.1 |
| CPf | CH3 | P | 4 | =O | 2.0 | 1.1 |
| CBd[b] | CH3 | B | 2 | =O | 0.01 | 0.011 |
| CBf | CH3 | B | 4 | =O | 5.6 | 2.8 |
| DPf | H | P | 4 | =O | 0.11 | 0.07 |
| DBd | H | B | 2 | =O | 0.04 | 0.021 |
| DBf | H | B | 4 | =O | 0.17 | 0.08 |
| BMf | CH3 | M | 4 | OH | 0.049 | 0.023 |
| CMf[a] | CH3 | M | 4 | =O | 0.023 | 0.011 |
| DMf[a] | H | M | 4 | =O | 0.010 | 0.0048 |

[a] HCl salt
[b] d-tartrate salt
B = cyclobutylmethyl
P = cyclopropylmethyl
M = methyl The compounds claimed herein, especially those with small $ED_{50}$ values, are very potent narcotic agonists. As such, they are useful for the relief of pain, for pre-operative anesthesia or for the immobilization of large animals. The dose to be administered to achieve the desired result, i.e., the effective dose, may vary from individual to individual but is readily determined by one skilled in the art without undue experimentation.

The compounds of the present invention form pharmacologically active addition salts with organic acids. Typical acid addition salts are the tartrate and maleate. These compounds may be administered by known conventional methods such as intravenous, parenteral, buccal, rectal or oral routes. Dose forms for the administration of these compounds can be prepared by methods recognized in the pharmaceutical sciences.

What is claimed is:

1. 7β-arylalkyl-7α-methyl-6-oxo or 6α-hydroxy-3-methoxy or 3-hydroxy-4,5α-epoxy-17-methyl or 17-cycloalkylmethyl-morphinans of the formula:

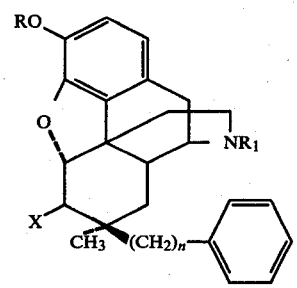

wherein R is H or methyl, X is oxo or α-hydroxy, n is 2 to 4 and R1 is methyl, cyclopropylmethyl or cyclobutylmethyl.

2. A compound as defined by claim 1 wherein R is methyl, X is α-hydroxy, n is 4 and $R_1$ is cyclopropylmethyl.

3. A compound as defined in claim 1 wherein R is methyl, X is α-hydroxy, n is 2 and $R_1$ is cyclobutylmethyl.

4. A compound as defined by claim 1 wherein R is methyl, X is oxo, n is 2 and $R_1$ is cyclobutylmethyl.

5. A compound as defined by claim 1 wherein R is H, X is oxo, n is 4 and $R_1$ is cyclopropylmethyl.

6. A compound as defined by claim 1 wherein R is H, X is oxo, n is 2 and $R_1$ is cyclobutylmethyl.

7. A compound as defined by claim 1 wherein R is H, X is oxo, n is 4 and $R_1$ is cyclobutylmethyl.

8. A compound as defined by claim 1 wherein R is methyl, X is α-hydroxy, n is 4 and $R_1$ is methyl.

9. A compound as defined by claim 1 wherein R is methyl, X is oxo, n is 4 and $R_1$ is methyl.

10. A compound as defined by claim 1 wherein R is H, X is oxo, n is 4 and $R_1$ is methyl.

* * * * *